(12) United States Patent
Jafari et al.

(10) Patent No.: US 11,701,522 B2
(45) Date of Patent: Jul. 18, 2023

(54) SYSTEM, METHODOLOGIES AND COMPONENTS FOR SKIN SCULPTING WITH MAGNETIC PARTICLES

(71) Applicant: Weinberg Medical Physics, Inc., North Bethesda, MD (US)

(72) Inventors: Sahar Jafari, North Bethesda, MD (US); Irving Weinberg, North Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 510 days.

(21) Appl. No.: 16/785,034

(22) Filed: Feb. 7, 2020

(65) Prior Publication Data

US 2020/0254273 A1 Aug. 13, 2020

Related U.S. Application Data

(60) Provisional application No. 62/802,386, filed on Feb. 7, 2019.

(51) Int. Cl.
*A61N 2/00* (2006.01)
*A61M 37/00* (2006.01)
*G01R 33/38* (2006.01)
*G01R 33/12* (2006.01)

(52) U.S. Cl.
CPC ............. *A61N 2/004* (2013.01); *A61M 37/00* (2013.01); *G01R 33/3808* (2013.01); *G01R 33/1276* (2013.01)

(58) Field of Classification Search
CPC ...................... A61B 2018/0047; A61N 1/406
See application file for complete search history.

(56) References Cited

U.S. PATENT DOCUMENTS

| | | | |
|---|---|---|---|
| 2005/0080446 A1 | 4/2005 | Gilson et al. | |
| 2014/0309479 A1* | 10/2014 | Weinberg | A61K 41/0028 600/12 |
| 2017/0227617 A1* | 8/2017 | Weinberg | G01R 33/381 |

FOREIGN PATENT DOCUMENTS

| | | |
|---|---|---|
| CN | 102695542 A | 9/2012 |
| TW | 201622773 A | 7/2016 |
| WO | WO-2008065652 A2 * | 6/2008 ......... A61B 18/1815 |

OTHER PUBLICATIONS

Chinese Office Action corresponding to CN202010082741.4 dated Jan. 30, 2023.

* cited by examiner

*Primary Examiner* — Kaylee R Wilson
(74) *Attorney, Agent, or Firm* — Barnes & Thornburg LLP

(57) ABSTRACT

A method, apparatus and components thereof enable stimulating synthesis of new collagen and elastic fibers in superficial tissues, of a human or other living subject by introducing magnetic particles into the superficial tissue and activating the magnetic particles by application of magnetic field to stimulate synthesis of new collagen and elastic fibers.

25 Claims, 5 Drawing Sheets

SYSTEM, METHODOLOGIES AND COMPONENTS FOR SKIN SCULPTING WITH MAGNETIC PARTICLES

CROSS REFERENCE AND PRIORITY CLAIM

This patent application claims priority to U.S. Provisional Patent Application No. 62/802,386, entitled "SKIN SCULPTING WITH MAGNETIC PARTICLES," filed Feb. 7, 2019, the disclosure of which being incorporated herein by reference in its entirety.

FIELD OF USE

Disclosed embodiments enable manipulation of magnetic particles for performing actions on superficial tissues, for example, cosmetic procedures and surgery.

BACKGROUND

Conventional techniques for reducing wrinkles include the heating of tissues (for example, through application of radio-frequency energy) to stimulate synthesis of new collagen and elastic fibers in superficial tissues, e.g., skin.

SUMMARY

Disclosed embodiments may disrupt collagen and elastic fibers and/or stimulate synthesis of new collagen and elastic fibers in superficial tissues to achieve a desired cosmetic effect.

In accordance with disclosed embodiments, an apparatus includes a controller and generator of magnetic fields coupled to one another and cooperating to apply magnetic field to one or more magnetic particles in the superficial tissue of a human or other living subject to move or activate the magnetic particles to disrupt collagen and elastic fibers and/or stimulate synthesis of new collagen and elastic fibers in the superficial tissue.

In accordance with disclosed embodiments, an apparatus may also include components configured to cooperate to image the magnetic particles in tissue to enable direction of injection, motion, guidance or activation of the one or more magnetic particles.

BRIEF DESCRIPTION OF THE FIGURES

The detailed description particularly refers to the accompanying figures in which.

DETAILED DESCRIPTION

Disclosed embodiments provide and application of this principle to provide technical utility for manipulation of at least one magnetic particle for the purposes of a medical or other practitioner to perform cosmetic operations on a human or other living body to stimulate synthesis of new collagen and elastic fibers in the skin. Disclosed embodiments are directed at providing an method, apparatus and components thereof for accomplishing this and related tasks.

Thus, disclosed embodiments may be implemented in whole or in part using an apparatus that includes a controller and generator of magnetic fields coupled together and configured to cooperate to apply magnetic field for moving and activating one or more magnetic particles in superficial tissue, e.g., skin. The apparatus may also include the magnetic particle(s) being moved or activated in the tissue.

In accordance with disclosed embodiments, an apparatus may also include components configured to cooperate to image the magnetic particle(s) in tissue to enable direction of injection, motion, guidance or activation of the one or more magnetic particles. Such a capability provides technical utility in the ability to analyze and control of direction of injection, motion, guidance or activation of particles.

Figure 5:
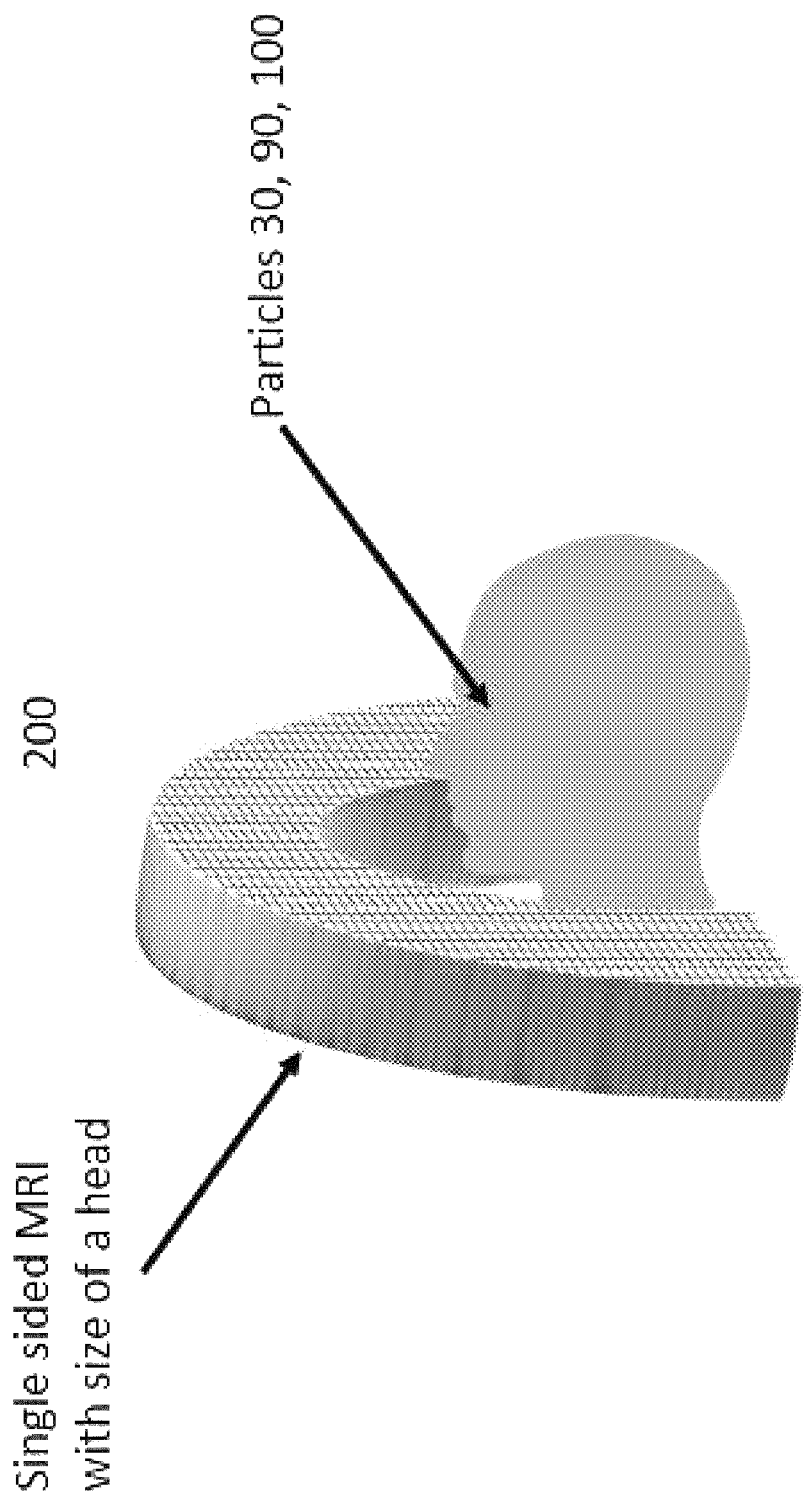
FIG. 5 illustrates an example of one implementation of the disclosed embodiments utilizing a single sided Magnetic Resonance Imaging (MRI) for treating a human patient with magnetic particles injected in the patient's face.

Such imaging may be performed with Magnetic Resonance Imaging, for example, by the controller and generator including electropermanent magnets to form a single-sided MRI, as has been described in US patent application 20170227617A1 by Irving Weinberg and Aleksandar Nacev (incorporated herein by reference). For example, FIG. 5 illustrates an example of one implementation of the disclosed embodiments utilizing a single sided Magnetic Resonance Imaging (MRI) for treating a human patient with magnetic particles injected in the patient's face.

It should be understood that electropermanent magnets and other sources of magnetic fields include but are not limited to "magnetoelectric material" or "magneto-electric material" or "magnetoelectric composite" or "magneto-electric composite," which encompass substances or combination of substances, in which changes in magnetic properties change in the presence of or application of an electric field.

Alternatively, imaging of the particle(s) and tissue could be performed with optical means, for example, provided the magnetic particles are visible optically (for example, the particles include a fluorescent material). Alternatively, imaging of the particle(s) could be accomplished with magnetic particle imaging. Alternatively, imaging of the tissue could be accomplished with ultrasound imaging.

Including imaging capability may have significant technical utility for a variety of reasons including to avoid damage to important tissue structures, for example, blood vessels or nerves resulting from transportation or other activation of particle(s), to guide the particle(s) to appropriate locations in the tissue (for example, near wrinkles), or to guide removal of the particles from the tissue following treatment of the tissue as discussed herein. Alternatively, or in addition, the particle(s) may be tethered to one another and/or to additional material or equipment to facilitate removal of the particle from tissue.

For the purposes of this disclosure, the terms "magnetic particles", "particles" and "magnetizable particles" are defined as one or more structures that can be magnetized at least in part using magnetic fields, where the maximum dimension of the structure of the particle is one millimeter or less. The magnetization of parts of the particle structures may be in different directions, as taught by Lamar Mair in US patent application U.S. Pat. No. 10,290,404, entitled "METHOD AND APPARATUS FOR NON-CONTACT AXIAL PARTICLE ROTATION AND DECOUPLED PARTICLE PROPULSION", incorporated herein by reference. Alternatively the magnetization of the particle structure may be uniform throughout the structure.

In accordance with disclosed embodiments, an apparatus includes a controller and generator of magnetic fields coupled to one another and cooperating to apply magnetic field to one or more magnetic particles in the superficial tissue of a human or other living subject to move or activate the magnetic particles to stimulate synthesis of new collagen and elastic fibers in the superficial tissue.

Figure 1:
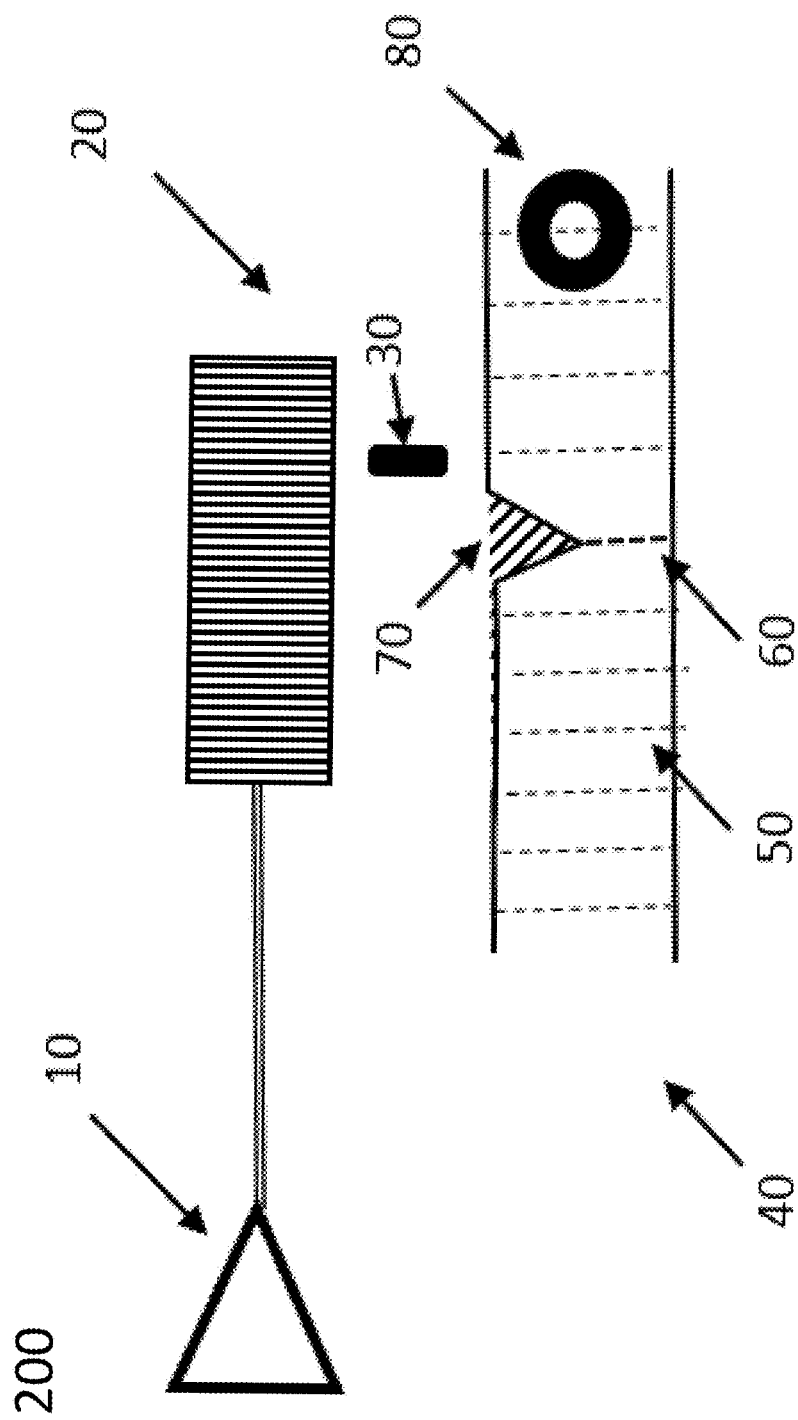
FIG. 1 illustrates an example of a disclosed embodiment wherein an apparatus contains at least one controller of electrical current or voltage that controls one or more generators of magnetic fields that manipulate at least one magnetic particle to affect superficial tissue of a human or other animal.

Thus, FIG. 1 illustrates an example of a disclosed embodiment an may be referenced to explained operations performed in conjunction with the disclosed embodiments. As shown in FIG. 1, an apparatus 200 may include at least one controller of electrical current or voltage 10 that is configured to control one or more generators 20 of magnetic fields. In FIG. 1, generator 10 may be implemented using an alternating current source suppling one or more electrical coils 20. Alternatively, generator 10 may be implemented using a current source supplying current to an array of electropermanent magnets 20.

The components of apparatus 200 may also include at least one magnetic particle 30 (and potentially a plurality of such magnetic particles 30). The magnetic particle(s) may be understood to be a structure less than a centimeter in maximum diameter in any dimension and containing at least one material that may be magnetized by an applied magnetic field. The magnetic particle may be less than a millimeter in minimal diameter.

In operations provided in accordance with disclosed embodiments, the apparatus 200 may be positioned in proximity or nearby to a superficial tissue 40 of a subject (for example a human or other animal). For the purposes of this specification, the term "proximity" and "nearby" are meant to mean less than 10 centimeters.

For the purposes of this specification, the term "superficial tissue" is meant to include tissues in which the thickness of the superficial tissue is less than 3-centimeters, and where at least some portion of the tissue is located less than 3-centimeters from the surface of the skin. The tissue may contain fibers (e.g. made of collagen and/or elastin), some of which having been stretched 50 by age or other physiological processes, and some of which having not been stretched 60. This combination of stretched and unstretched fibers may cause the appearance of indentations or wrinkles 70 in the skin.

As mentioned above, including imaging capability may have significant technical utility for a variety of reasons including to avoid damage to important tissue structures, for example, blood vessels or nerves 80 resulting from transportation or other activation of particle(s).

Figure 2:
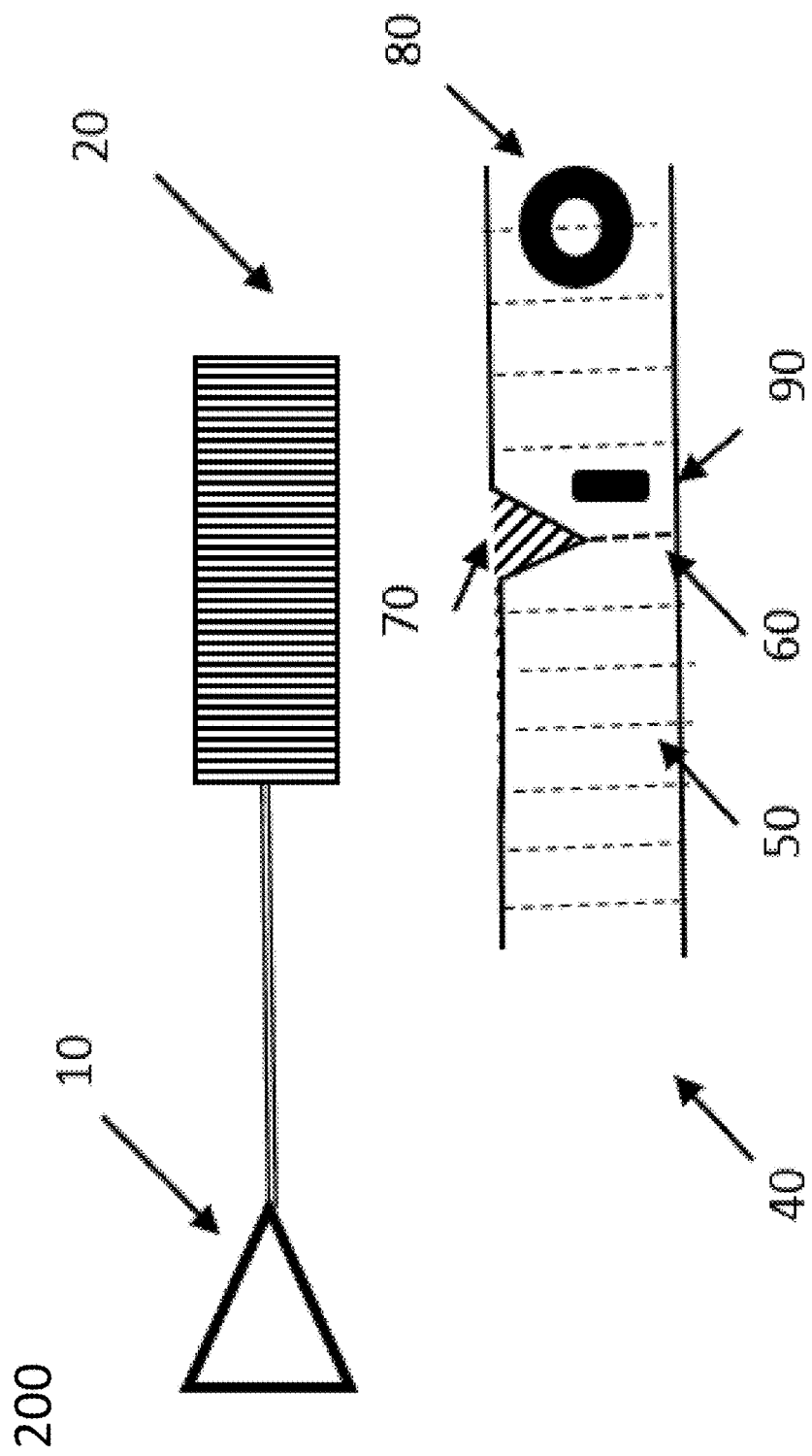
FIG. 2 illustrates an example of the at least one magnetic particle inserted into the superficial tissue after being transported to a different position in accordance with the disclosed embodiments.

FIG. 2 illustrates that particle(s) previously referenced as particle 30 in FIG. 1, after the particle has been inserted into tissue 40 and is now located in a different position. Thus, in FIG. 2, the repositioned particle is referenced as particle 90.

This insertion may have been accomplished with an injection, for example, manually via a syringe containing a solution including the particle(s). Alternatively, the insertion may have been through a skin incision made with a scalpel or other sharp instrument. Thus, in accordance with at least some embodiments, the particle(s) 30 may be injected into tissue 40. In one example, this may be accomplished with magnetic fields, using rotation, as described by the publication by Sahar Jafari et al entitled "Intra-nasal transport of particles into rodent brain by magnetic drilling", Journal of Magnetism and Magnetic Materials (2018). 10.1016/j.jmmm.2018.08.048.

Additionally or alternatively movement and/or injection of the particles may be accomplished with magnetic propulsion, for example, as described by Irving Weinberg et al in U.S. Pat. No. 9,694,196, entitled "SYSTEM, METHOD, AND EQUIPMENT FOR IMPLEMENTING TEMPORARY DIAMAGNETIC PROPULSIVE FOCUSING EFFECT WITH TRANSIENT APPLIED MAGNETIC FIELD PULSES", incorporated herein by reference.

Activation of the particle(s), e.g., rotation, vibration, heating or otherwise, of particle(s) (referenced as particle 30, 90 or 100) may be accomplished with magnetic torques and/or forces applied by the controller 10 and the generator of magnetic fields 20. For example, activation such as rotation may disrupt tissue fibers (referenced as 60 or 100) in order to reduce the depth of wrinkle 70, 120. The particle(s) (reference as particle 30, 90 or 100) may also reduce the depth of wrinkle 70, 120 through other means, for example, heating of the tissue via magnetic induction or other magnetic means, or as a result of a drug or other chemical agent previously loaded on or in the particle(s) and released by the particle(s). That release could be due to magnetic activation, for example, heating. Such drugs or other chemical agents may include, for example, what are known as collagen-stimulating fillers, which contain microscopic particles that prompt the superficial tissue to make new collagen, which can result in smoother skin and volume.

Figure 3:
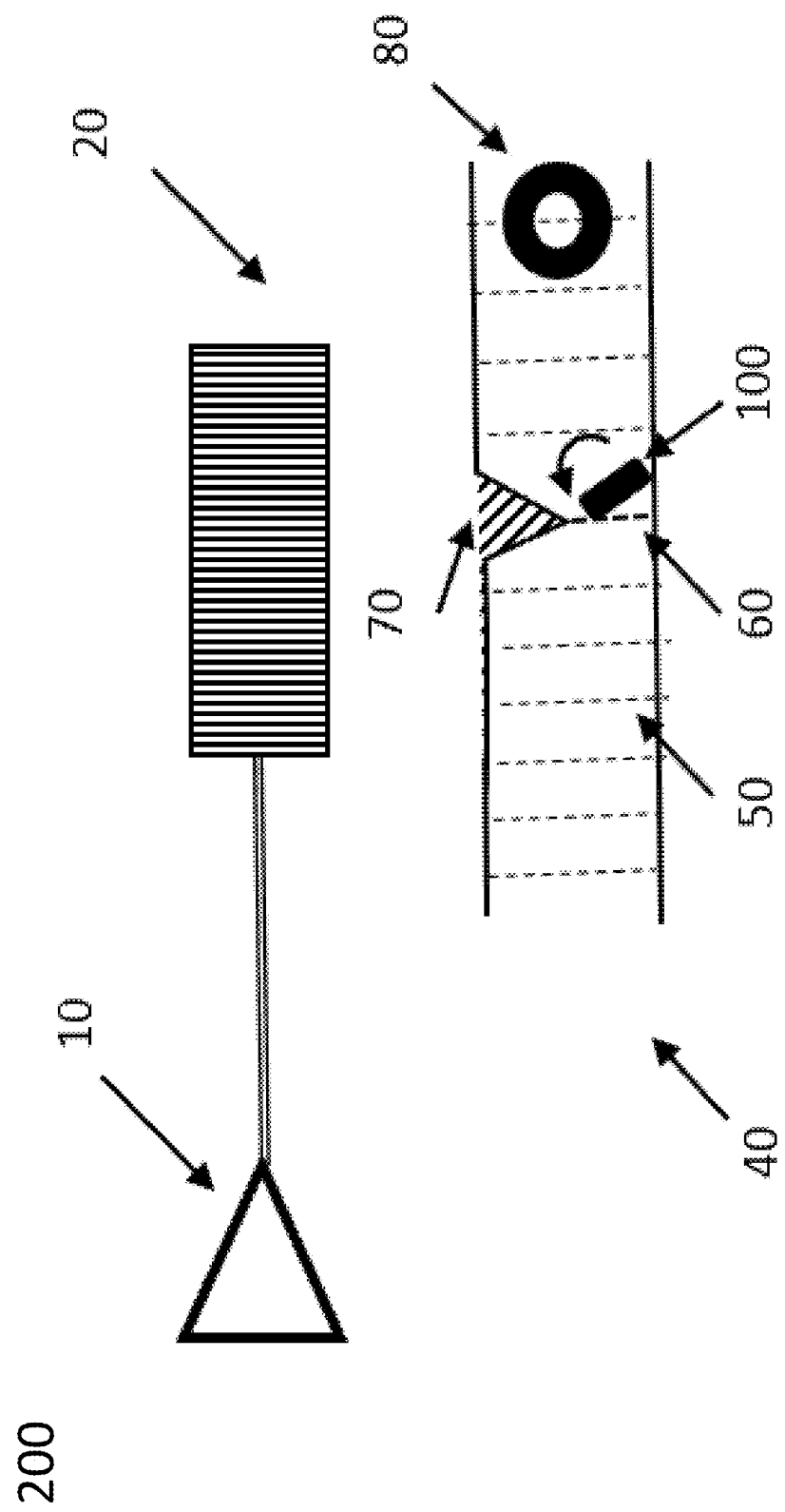
FIG. 3 illustrates an example of the at least one magnetic particle following rotation or otherwise activation by application of magnetic forces, torques, or induced currents in accordance with the disclosed embodiments.

Accordingly, FIG. 3 shows that particle(s) previously described as particle 30 in FIG. 1 and particle 90 in FIG. 2 has been rotated or otherwise activated (for example, by induction heating) and is now referenced as particle 100. This rotation and/or activation may have been accomplished with magnetic forces, torques, or induced currents created or modified by controller 10 and generator 20.

Figure 4:
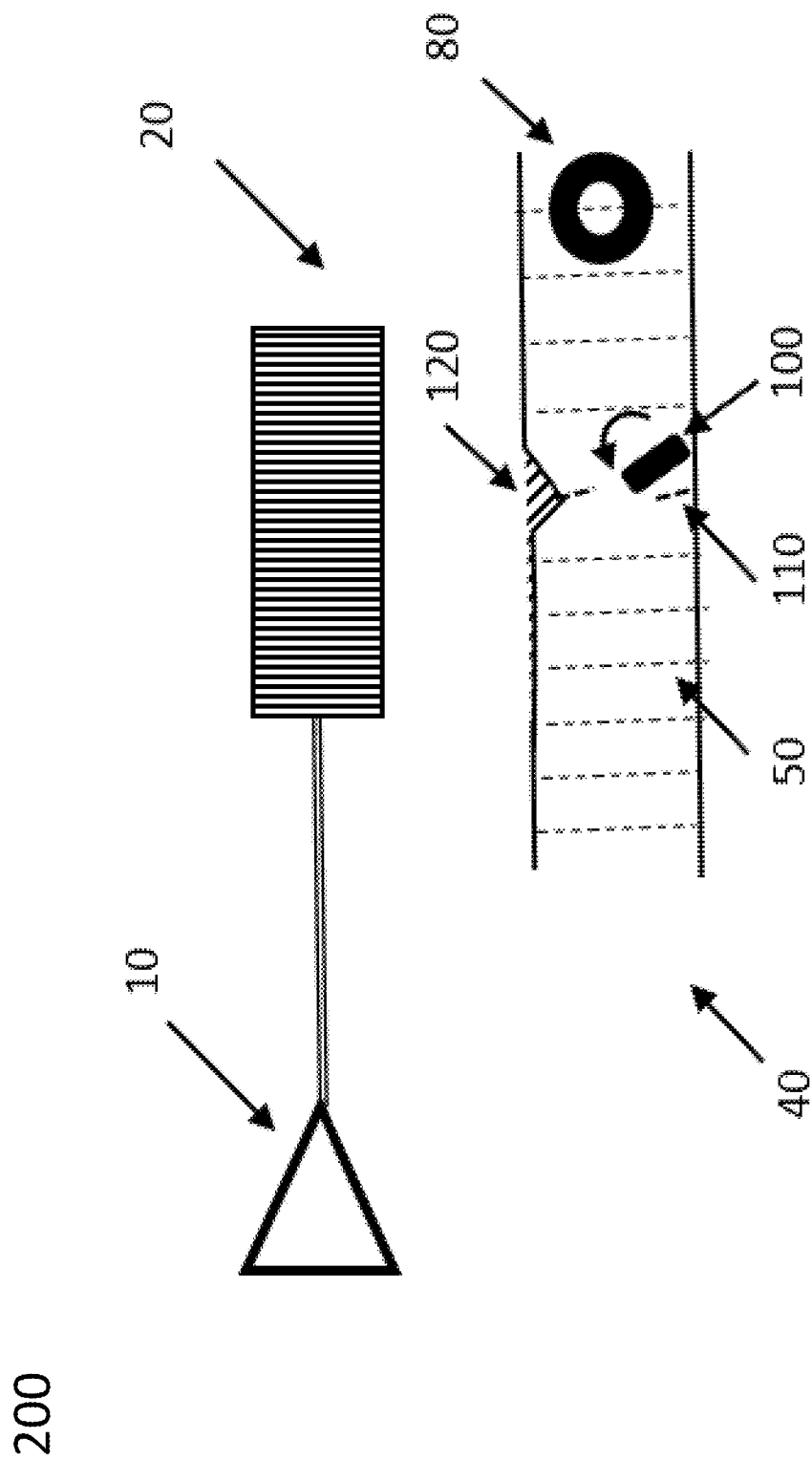
FIG. 4 illustrates an example of a potential effect of the rotation or otherwise activation on the superficial tissue in accordance with the disclosed embodiments.

FIG. 4 shows that the activation of the particles previously described as 100 may have disrupted the fiber previously referenced as fiber 60. Thus, the new disrupted fiber is now denoted as 110. As a result of this disruption, the wrinkle indentation previously referenced as indentation 70 may be reduced in size or eliminated and is now denoted as indentation 120.

Following completion of procedures using the particle(s) within the tissue, the particle(s) could be removed from the tissue 40 by the apparatus 200 through drilling motion, similar to the manner in which they were injected into the tissue. It should also be understood that at least some or all of the particle(s) could be eliminated from the tissue 40 via biodegradation of the particle(s). The particle(s) may be attached to a string or catheter or other tethering structure enabling or assisting withdrawal of the particle from the tissue.

Those skilled in the art will recognize, upon consideration of the above teachings, that the above exemplary embodiments may perform the above-specified operations (and those referred in the claims) under the control of at least one controller that may utilize or be based upon use of one or more programmed processors programmed with a suitable computer program. However, the disclosed embodiments could utilize one or more controllers implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Furthermore, it should be understood that control and cooperation of components of an apparatus for applying magnetic fields described herein to manipulate the one or more particles may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

The invention claimed is:

1. A system for affecting superficial tissue in a live subject, the system comprising:
    a plurality of magnetic particles configured to be injected into the superficial tissue, wherein at least one magnetic particle of the plurality of magnetic particles includes a tether to facilitate removal of the particle from the superficial tissue;
    a power source configured to provide electrical power;
    a magnetic field generator coupled to the power source to receive power to generate a magnetic field; and
    a controller coupled to the power source and the magnetic field generator to control the power source and the magnetic field generator to produce the magnetic field in the proximity of the superficial tissue,
    wherein the at least one part of at least one magnetic particle of a plurality of magnetic particles injected into the superficial tissue is activated by the magnetic field, and
    wherein the controller is configured to affect superficial tissue by moving the at least one magnetic particle within the superficial tissue by application of the generated magnetic field to produce a desired cosmetic effect by disrupting collagen or elastic fibers in the superficial tissue via the movement.

2. The system of claim 1, wherein the desired cosmetic effect is removal or reduction of an appearance of at least one wrinkle.

3. The system of claim 1, further comprising a mechanism for injecting the plurality of magnetic particles into the superficial tissue.

4. The system of claim 3, wherein the mechanism for injecting the plurality of magnetic particles into the superficial tissue is a syringe containing a solution including the plurality of magnetic particles.

5. The system of claim 3, wherein the mechanism for injecting the plurality of magnetic particles into the superficial tissue applies magnetic fields, using rotation, to perform magnetic drilling.

6. The system of claim 3, wherein the mechanism for injecting the plurality of magnetic particles into the superficial tissue uses temporary diamagnetic propulsive focusing of the plurality of magnetic particles by applying transient magnetic field pulses to the superficial tissue.

7. The system of claim 1, wherein the power source, controller and magnetic field generator are incorporated in a one-sided magnetic resonance imaging system.

8. The system of claim 1, further comprising an imaging system for imaging the at least one magnetic particle of the plurality of magnetic particles to monitor movement and/or activation of the at least one particle.

9. The system of claim 8, wherein imaging of the at least one magnetic particle of the plurality of magnetic particles in tissue is used to avoid damage to important tissue structures.

10. The system of claim 1, wherein the activation of the at least one part of the at least one magnetic particle of the plurality of magnetic particles are configured to rotate the at least one magnetic particle in the superficial tissue to disrupt tissue fibers.

11. The system of claim 1, wherein the activation of the at least one part of the at least one magnetic particle of the plurality of magnetic particles are configured to heat the tissue via magnetic induction applied to the at least one magnetic particle in the superficial tissue to disrupt tissue fibers.

12. The system of claim 1, wherein the activation of the at least one part of the at least one magnetic particle of the plurality of magnetic particles are configured to release a drug or other chemical agent loaded on or in the at least one magnetic particle in response to magnetic activation.

13. A method for affecting superficial tissue in a live subject to achieve a desired cosmetic effect, the method comprising:
    generating a magnetic field using a power source coupled to a magnetic field generator under control of a controller to produce a magnetic field in proximity to the superficial tissue;
    positioning a plurality of magnetic particles within the superficial tissue;

activating, by the magnetic field, at least one part of at least one magnetic particle of the plurality of magnetic particles in the superficial tissue;

moving the at least one magnetic particle within the superficial tissue by application of the generated magnetic field; and disrupting collagen or elastic fibers in the superficial tissue via the movement to achieve the desired cosmetic effect.

14. The method of claim 13, wherein the desired cosmetic effect is removal or reduction of an appearance of at least one wrinkle.

15. The method of claim 13, wherein positioning the at least one magnetic particle of the plurality of magnetic particles within the superficial tissue comprises injecting the plurality of magnetic particles into the superficial tissue.

16. The method of claim 15, wherein injecting the plurality of magnetic particles into the superficial tissue comprises using a syringe containing a solution including the plurality of magnetic particles.

17. The method of claim 15, wherein injecting the plurality of magnetic particles into the superficial tissue comprises applying magnetic fields, using rotation, to perform magnetic drilling.

18. The method of claim 15, wherein injecting the plurality of magnetic particles into the superficial tissue uses temporary diamagnetic propulsive focusing of the plurality of magnetic particles by applying transient magnetic field pulses to the superficial tissue.

19. The method of claim 13, wherein the power source, controller and magnetic field generator are incorporated in a one-sided magnetic resonance imaging system.

20. The method of claim 13, further comprising imaging the at least one magnetic particle of the plurality of magnetic particles to monitor movement and/or activation of the at least one magnetic particle.

21. The method of claim 20, wherein imaging of the at least one magnetic particle of the plurality of magnetic particles in tissue is used to avoid damage to important tissue structures.

22. The method of claim 13, wherein the activation of the at least one part of the at least one magnetic particle of the plurality of magnetic particles rotates the at least one magnetic particle in the superficial tissue to disrupt tissue fibers.

23. The method of claim 13, wherein the activation of the at least one part of the at least one magnetic particle of the plurality of magnetic particles heats the tissue via magnetic induction applied to the at least one magnetic particle in the superficial tissue to disrupt tissue fibers.

24. The method of claim 13, wherein the activation of the at least one part of the at least one magnetic particle of the plurality of magnetic particles releases a drug or other chemical agent loaded on or in the at least one magnetic particle in response to magnetic activation.

25. The method of claim 13, wherein the at least one magnetic particle of the plurality of magnetic particles is tethered to facilitate removal of the at least one magnetic particle of the plurality of magnetic particles from the superficial tissue.

* * * * *